(12) United States Patent
Liu et al.

(10) Patent No.: US 6,929,729 B2
(45) Date of Patent: Aug. 16, 2005

(54) METHOD FOR CONDUCTING CAPILLARY ZONE ELECTROPHORESIS

(75) Inventors: ChangSheng Liu, State College, PA (US); Kevin J. Levan, State College, PA (US)

(73) Assignee: SpectruMedix LLC, State College, PA (US)

( * ) Notice: Subject to any disclaimer, the term of this patent is extended or adjusted under 35 U.S.C. 154(b) by 353 days.

(21) Appl. No.: 09/757,632

(22) Filed: Jan. 11, 2001

(65) Prior Publication Data

US 2001/0047940 A1 Dec. 6, 2001

Related U.S. Application Data

(60) Provisional application No. 60/177,652, filed on Jan. 27, 2000.

(51) Int. Cl.$^7$ .................. G01N 27/26; G01N 27/447; B01D 57/02
(52) U.S. Cl. ............. 204/451; 204/453; 204/601
(58) Field of Search ................. 204/451, 453, 204/601

(56) References Cited

U.S. PATENT DOCUMENTS

| | | | | |
|---|---|---|---|---|
| 4,997,536 A | * | 3/1991 | Ohms et al. ........... | 204/454 |
| 5,124,020 A | * | 6/1992 | Wang .................. | 204/452 |
| 5,459,272 A | * | 10/1995 | Novotny et al. ....... | 546/168 |
| 5,792,330 A | * | 8/1998 | Petersen et al. ...... | 204/452 |

FOREIGN PATENT DOCUMENTS

JP     8-114575     * 5/1996

OTHER PUBLICATIONS

Kenndler et al, Journal of Chromatography, 545, (1991), pp. 397–402.*

Hu et al, Journal of Chromatography A, 717, (1995), pp. 33–39.*

* cited by examiner

Primary Examiner—Alan Diamond
(74) Attorney, Agent, or Firm—Fish & Richardson P.C.

(57) ABSTRACT

A method for conducting capillary zone electrophoresis in which a lubricating detergent is added to help prevent sample buildup on the inner walls of the capillary. In a preferred embodiment the lubricating detergent is sodium dodecylsulfate (SDS) in a concentration of about 3 mM added to a protein sample before the sample is introduced into one end of a capillary. The SDS may be added to the buffer, instead of the sample, before electrophoresis.

22 Claims, 2 Drawing Sheets

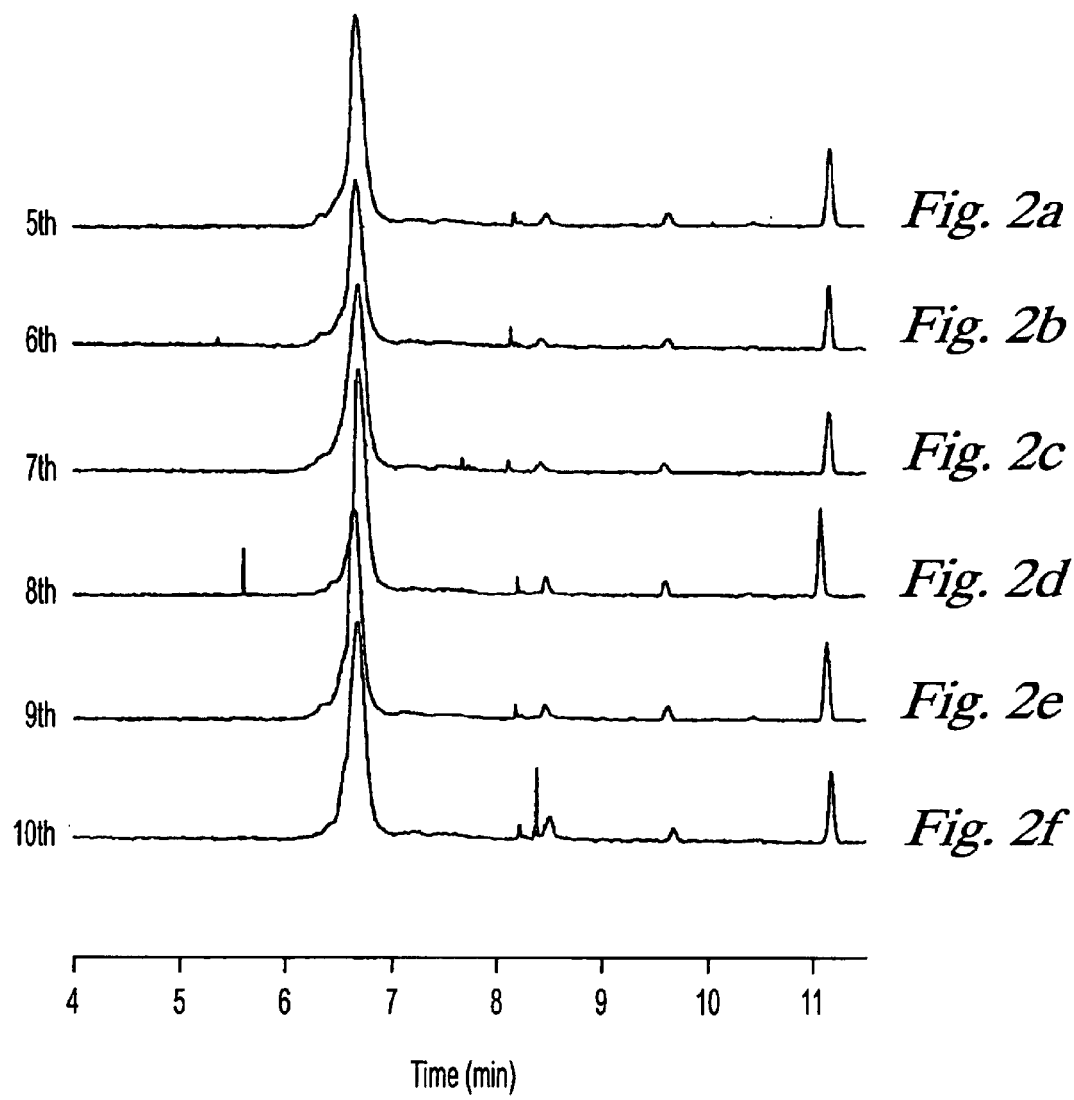

METHOD FOR CONDUCTING CAPILLARY ZONE ELECTROPHORESIS

RELATED APPLICATIONS

The present application claims priority to U.S. Provisional Application No. 60/177,652, filed Jan. 27, 2000.

TECHNICAL FIELD

The present invention is directed to the general area of capillary zone electrophoresis. More particularly, it is directed to additives which extend the life of a capillary so that it can be used for several electrophoresis runs while still providing good separation resolution and reproducible results from run to run.

BACKGROUND

FIG. 1 shows a typical arrangement 100 for conducting capillary electrophoresis. A capillary 102 having a window region 104 has its ends dipped in buffer 106. A sample 108 to be electrophoresced is introduced at one of the capillary's ends and a voltage differential is applied across the two ends. This causes the sample 108 to separate into its components, each of which migrate at different rates in the direction depicted by the arrow. A laser light source 110 is used to illuminate the samples, which typically are tagged with a chromophore. In response to this excitation, the samples emit light 112 which is then captured by a camera 114, after which the results are processed by a computer 116.

In the configuration described, the capillaries are used a number of times before they are discarded. Without some form of capillary cleaning, however, a small quantity of a sample, such as protein, may get absorbed on the inner wall of the capillary, thereby contaminating a subsequent electrophoresis run. Therefore, between each electrophoresis run, a capillary is typically rinsed, usually under high pressure. Although a variety of cleaning solutions may be employed to rinse a capillary, one of the more popular rinses is NaOH, such as in the concentration of 50 mM to 200 mM. The NaOH solution is pumped through the capillaries to help remove residual traces of the electrophoretic medium and the sample which migrated therein.

SUMMARY OF THE INVENTION

The present invention is realized by adding a predetermined quantity of a lubricating detergent to at least one of the buffer and the sample to be separated before a capillary electrophoresis run. In a preferred embodiment, the lubricating detergent is a sodium dodecylsulfate (SDS) solution.

BRIEF DESCRIPTION OF THE DRAWINGS

The present invention can better be understood through the attached figures in which:

FIG. 2 shows experimental results demonstrating the repeatability of results using the present invention.

DETAILED DESCRIPTION OF THE PREFERRED EMBODIMENT

Figure 1:
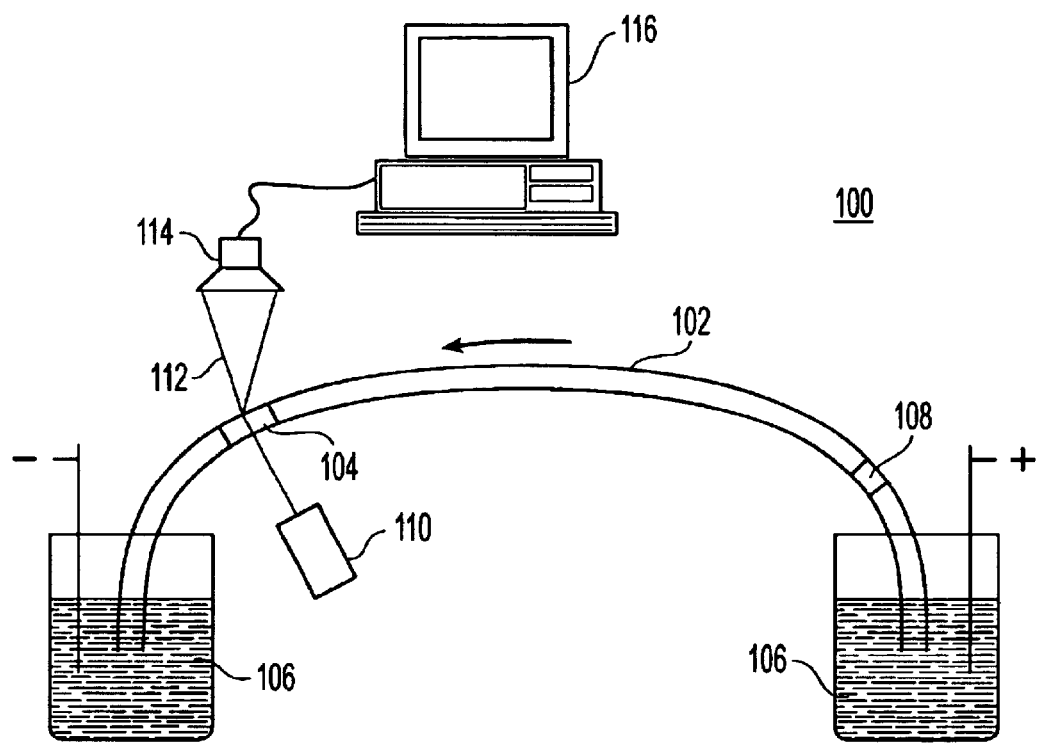
FIG. 1 shows the prior art environment in which the present invention may be used.

Experiments were run to evaluate the use of SDS. The configuration of the equipment was as follows: Multiple parallel capillaries were used. Each capillary had an inner diameter of 50 $\mu$m, and outer diameter of 150 $\mu$m, and a total length of 50 cm, with an effective length of 40 cm from the sample end to the window detection region through which light from a chromophore associated with the sample, can be detected. Excitation was provided by an all-length 200 mW AR-ion laser shining at the capillaries. A CCD camera configured substantially in the manner disclosed in U.S. Pat. No. 5,998,796, captured the spectra-resolved images. The voltage applied across the capillary ends was ±10 kV at the injection end. i.e., +200 V/cm. The buffer used during electrophoresis was 10 mM borate acid having a pH of 10.5. Finally, the protein sample was injected at the injection end using a vacuum at −0.5 psi for 5 seconds.

FIG. 2 shows the experimental results of capillary zone electrophoresis when SDS in a concentration of 3 mM is added to a protein sample with no NaOH rinsing between runs. In FIG. 2, the six plots correspond to the $5^{th}$–$10^{th}$ runs of a single capillary which had previously undergone four electrophoresis runs. As seen in this figure, the relative positions of the various significant peaks within a single plot is substantially the same across the six plots. Therefore, FIG. 2 demonstrates the reproducibility of results among the successive runs using the same protein sample with a single capillary.

While the present invention has been described with reference to certain preferred embodiments, it should be kept in the mind that variations of these embodiments are also within the scope of the present invention. For example, SDS may be added in a concentration other than that used in the examples. In general, the concentration of SDS should below its critical micelle concentration of 8 mM. And instead of adding the SDS to the protein sample, the SDS may instead be present in the buffer at the sample end.

What is claimed is:

1. A method for conducting capillary zone electrophoresis in a capillary, the method comprising:

adding sodium dodecylsulfate (SDS) to a first sample to be electrophoresced;

injecting the first sample into a first end of said capillary;

applying a first voltage differential across said first end of said capillary and a second end of said capillary to cause said first sample to migrate in a medium suitable for capillary zone electrophoresis;

adding SDS to a second sample to be electrophoresced;

injecting said second sample into said first end of said capillary without rinsing said capillary with a cleaning solution intermediate the steps of applying a first voltage and injecting a second sample; and applying a second voltage differential across said first and second ends of said capillary to cause said second sample to migrate in said medium suitable for capillary zone electrophoresis.

2. The method of claim 1, wherein a concentration of SDS is below its critical micelle concentration of 8 mM.

3. A method for conducting capillary zone electrophoresis in a capillary, the method comprising:

adding sodium dodecylsulfate (SDS) to a first sample to be electrophoresced;

applying a first voltage differential across ends of said capillary to cause said first sample to migrate in a medium suitable for capillary zone electrophoresis;

adding SDS to a second sample to be electrophoresced; and applying a second voltage differential across ends of said capillary to cause said second sample to migrate, without rinsing the capillary with a cleaning solution between application of said first and second voltage differentials.

4. A method for conducting capillary zone electrophoresis in a capillary having first and second ends, the method comprising:
- providing a sodium dodecylsulfate (SDS)-containing buffer for receiving the first end of the capillary;
- applying a first voltage differential across the first and second ends to cause a first sample in said capillary to migrate in a medium suitable for capillary zone electrophoresis;
- injecting a second sample into said first end of said capillary without rinsing said capillary with a cleaning solution intermediate the steps of applying a first voltage and injecting a second sample; and
- applying a second voltage differential across the first and second ends to cause the second sample to migrate in the medium suitable for capillary zone electrophoresis.

5. A method for conducting electrophoresis in a capillary having first and second ends, the method comprising:
- injecting into the first end of the capillary a first sample;
- subjecting the first sample to electrophoresis in the presence of a buffer comprising sodium dodecylsulfate (SDS), the step of subjecting comprising:
  - contacting the first end of the capillary with a volume of the buffer; and
  - applying a first voltage differential across the first and second ends of the capillary;
- after application of the first voltage differential, injecting into the first end of the capillary a second sample; and
- subjecting the second sample to electrophoresis in the presence of a second buffer comprising SDS, the step of subjecting the second sample to electrophoresis comprising:
  - contacting the first end of the capillary with a volume of the second buffer; and
  - applying a second voltage differential across the first and second ends of the capillary without rinsing the capillary with a cleaning solution intermediate the application of the first and second voltage differentials.

6. The method of claim 5, further comprising:
after application of the second voltage differential:
- injecting into the first end of the capillary a third sample; and
- subjecting the third sample to electrophoresis in the presence of a third buffer comprising SDS, the step of subjecting the third sample to electrophoresis comprising:
  - contacting the first end of the capillary with a volume of the third buffer; and
  - applying a third voltage differential across the first and second ends of the capillary without rinsing the capillary with a cleaning solution intermediate the application of the first and third voltage differentials.

7. The method of claim 6, further comprising:
after application of the third voltage differential:
- injecting into the first end of the capillary a fourth sample; and
- subjecting the fourth sample to electrophoresis in the presence of a fourth buffer comprising SDS, the step of subjecting the fourth sample to electrophoresis comprising:
  - contacting the first end of the capillary with a volume of the fourth buffer; and
  - applying a fourth voltage differential across the first and second ends of the capillary without rinsing the capillary with a cleaning solution intermediate the application of the first and fourth voltage differentials.

8. The method of claim 6, wherein each of the first, second, and third buffers is a borate buffer.

9. The method of claim 5, wherein a concentration of the SDS in the first and second buffers is less than a critical micelle concentration of the SDS in the first and second buffers.

10. The method of claim 5, wherein a ratio of each of the first and second voltage differentials to a length between the first and second ends of the capillary is +200 V/cm.

11. A method for conducting electrophoresis in a capillary having first and second ends, the method comprising:
- injecting into the first end of the capillary a first sample;
- subjecting the first sample to electrophoresis in the presence of a buffer comprising a lubricating detergent, the step of subjecting comprising:
  - contacting the first end of the capillary with a volume of the buffer; and
  - applying a first voltage differential across the first and second ends of the capillary;
- after application of the first voltage differential, injecting into the fist end of the capillary a second sample; and
- subjecting the second sample to electrophoresis in the presence of a second buffer comprising the lubricating detergent, the step of subjecting the second sample to electrophoresis comprising:
  - contacting the first end of the capillary with a volume of the second buffer; and
  - applying a second voltage differential across the first and second ends of the capillary without rinsing the capillary with a cleaning solution intermediate the application of the first and second voltage differentials.

12. The method of claim 11, further comprising:
after application of the second voltage differential:
- injecting into the first end of the capillary a third sample; and
- subjecting the third sample to electrophoresis in the presence of a third buffer comprising the lubricating detergent, the step of subjecting the third sample to electrophoresis comprising:
  - contacting the first end of the capillary with a volume of the third buffer; and
  - applying a third voltage differential across the first and second ends of the capillary without rinsing the capillary with a cleaning solution intermediate the application of the first and third voltage differentials.

13. The method of claim 12, further comprising:
after application of the third voltage differential:
- injecting into the first end of the capillary a fourth sample; and
- subjecting the fourth sample to electrophoresis in the presence of a fourth buffer comprising the lubricating detergent, the step of subjecting the fourth sample to electrophoresis comprising:
  - contacting the first end of the capillary with a volume of the fourth buffer; and
  - applying a fourth voltage differential across the first and second ends of the capillary without rinsing the capillary with a cleaning solution intermediate the application of the first and fourth voltage differentials.

14. The method of claim 11, wherein each of the first, second, and third buffers is a borate buffer.

15. The method of claim 11, wherein a ratio of each of the first and second voltage differentials to a length between the first and second ends of the capillary is +200 V/cm.

16. A method for conducting electrophoresis, comprising:

subjecting a first sample to electrophoresis within a capillary and in the presence of sodium dodecylsulfate (SDS); and subjecting a second sample to electrophoresis within the capillary and in the presence of SDS without rinsing the capillary with a cleaning solution intermediate the steps of subjecting the first sample to electrophoresis and subjecting the second sample to electrophoresis.

17. The method of claim 16, further comprising:

after subjecting the second sample to electrophoresis, subjecting a third sample to electrophoresis within the capillary and in the presence of SDS without rinsing the capillary with a cleaning solution intermediate the steps of subjecting the first sample to electrophoresis and subjecting the third sample to electrophoresis.

18. The method of claim 17, further comprising:

after subjecting the third sample to electrophoresis, subjecting a fourth sample to electrophoresis within the capillary and in the presence of SDS without rinsing the capillary with a cleaning solution intermediate the steps of subjecting the first sample to electrophoresis and subjecting the fourth sample to electrophoresis.

19. The method of claim 16, wherein the SDS is present at a concentration of less than a critical micelle concentration of the SDS.

20. A method for conducting electrophoresis, comprising:

subjecting a first sample to electrophoresis within a capillary and in the presence of a lubricating detergent; and subjecting a second sample to electrophoresis within the capillary and in the presence of the lubricating detergent without rinsing the capillary with a cleaning solution intermediate the steps of subjecting the first sample to electrophoresis and subjecting the second sample to electrophoresis.

21. The method of claim 20, further comprising:

after subjecting the second sample to electrophoresis, subjecting a third sample to electrophoresis within the capillary and in the presence of the lubricating detergent without rinsing the capillary with a cleaning solution intermediate the steps of subjecting the first sample to electrophoresis a and subjecting the third sample to electrophoresis.

22. The method of claim 21, further comprising:

after subjecting the third sample to electrophoresis, subjecting a fourth sample to electrophoresis within the capillary and in the presence of the lubricating detergent without rinsing the capillary with a cleaning solution intermediate the steps of subjecting the first sample to electrophoresis and subjecting the fourth sample to electrophoresis.

* * * * *